(12) United States Patent
Pisarnwongs et al.

(10) Patent No.: US 8,795,294 B2
(45) Date of Patent: Aug. 5, 2014

(54) DELIVERY MECHANISM FOR TISSUE HOLDING IMPLANTS

(75) Inventors: Roger Pisarnwongs, Valencia, CA (US); Thomas Weisel, Ventura, CA (US)

(73) Assignee: Arch Day Design, LLC, Ventura, CA (US)

( * ) Notice: Subject to any disclaimer, the term of this patent is extended or adjusted under 35 U.S.C. 154(b) by 1004 days.

(21) Appl. No.: 12/417,998

(22) Filed: Apr. 3, 2009

(65) Prior Publication Data

US 2009/0254102 A1 Oct. 8, 2009

Related U.S. Application Data

(60) Provisional application No. 61/123,077, filed on Apr. 4, 2008.

(51) Int. Cl.
*A61B 17/04* (2006.01)
*A61B 17/12* (2006.01)
*A61B 17/068* (2006.01)
*A61B 17/00* (2006.01)
*A61B 17/10* (2006.01)

(52) U.S. Cl.
CPC ... *A61B 17/0682* (2013.01); *A61B 2017/00867* (2013.01); *A61B 17/105* (2013.01)
USPC .......................................................... 606/143

(58) Field of Classification Search
USPC ................ 606/139, 142–144, 151, 157, 228; 227/175.1, 176.1, 177.1, 178.1, 179.1
See application file for complete search history.

(56) References Cited

U.S. PATENT DOCUMENTS

| | | | | | |
|---|---|---|---|---|---|
| 4,372,316 | A | * | 2/1983 | Blake et al. | 606/143 |
| 4,450,840 | A | * | 5/1984 | Mericle et al. | 606/143 |
| 4,821,721 | A | * | 4/1989 | Chin et al. | 606/143 |
| 5,190,560 | A | * | 3/1993 | Woods et al. | 606/137 |
| 5,431,669 | A | * | 7/1995 | Thompson et al. | 606/143 |
| 5,997,552 | A | * | 12/1999 | Person et al. | 606/139 |
| 6,423,079 | B1 | * | 7/2002 | Blake, III | 606/143 |
| 7,547,326 | B2 | * | 6/2009 | Bhatnagar et al. | 623/17.16 |
| 2002/0099388 | A1 | * | 7/2002 | Mayenberger | 606/139 |
| 2003/0023250 | A1 | * | 1/2003 | Watschke et al. | 606/148 |
| 2005/0131429 | A1 | * | 6/2005 | Ho et al. | 606/143 |

OTHER PUBLICATIONS

"Channel" definition from TheFreeDictionary.com <http://www.thefreedictionary.com/channel>.*

* cited by examiner

*Primary Examiner* — Katherine M Shi
(74) *Attorney, Agent, or Firm* — Koppel, Patrick, Heybl & Philpott

(57) ABSTRACT

A delivery mechanism for delivering tissue holding implants through tissues to be held in approximation includes a shaft having a tip at its distal end, and which is loaded with one or more implants. A wire channel which contains a driving wire is also located within the shaft. When the mechanism is actuated, the driving wire exhibits a proportional longitudinal displacement in the wire channel, such that the wire engages an implant, conveys it along the shaft's longitudinal axis towards the tip, and forces it through the tip. The implants are oriented such that they lie along or nearly along the shaft's longitudinal axis when being conveyed along the axis. The mechanism may optionally include an opposing jaw arranged such that, when actuated, the distal end of the jaw is moved towards the tip, such that tissues placed between the jaw and tip are pinned between them.

13 Claims, 14 Drawing Sheets

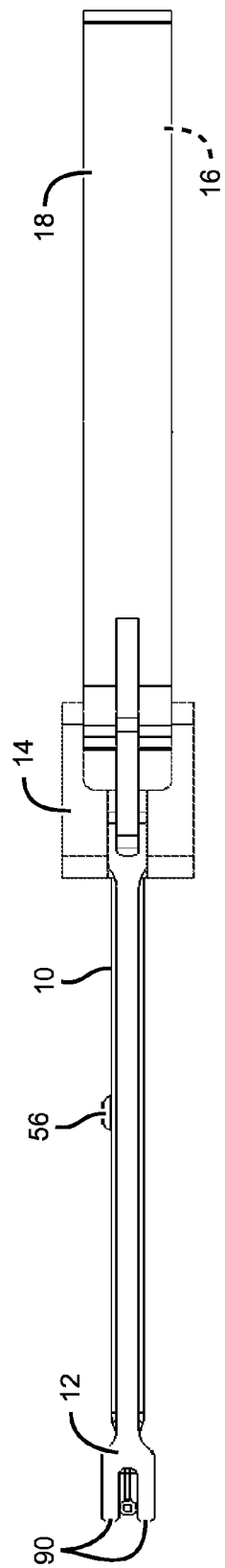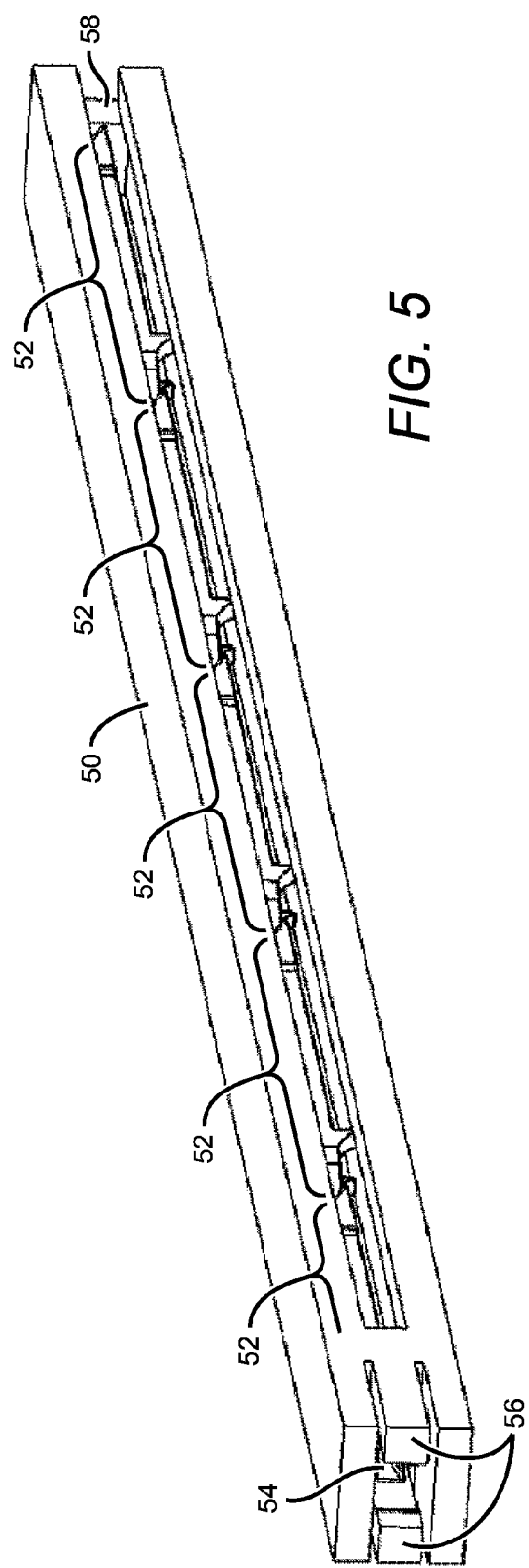

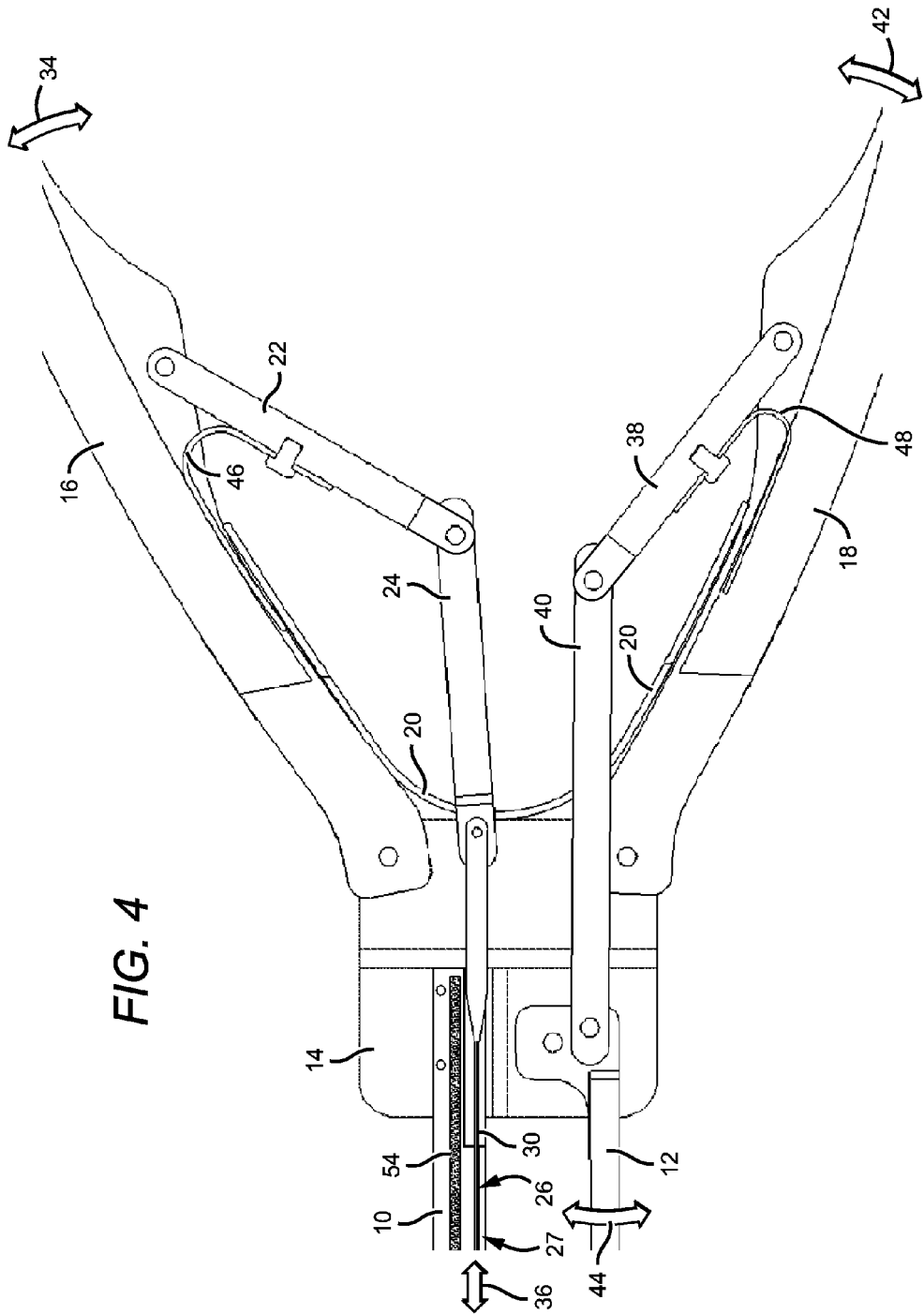

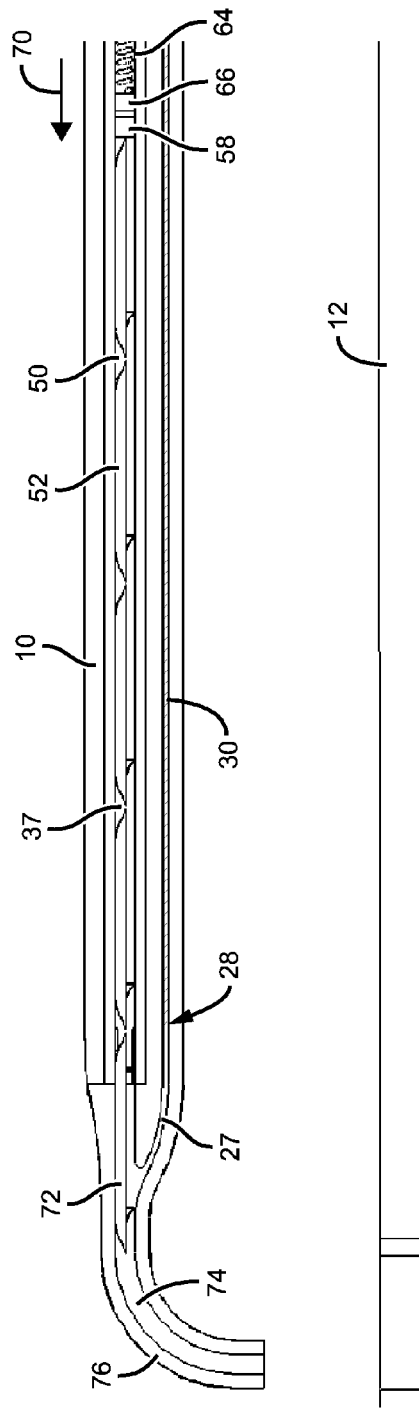
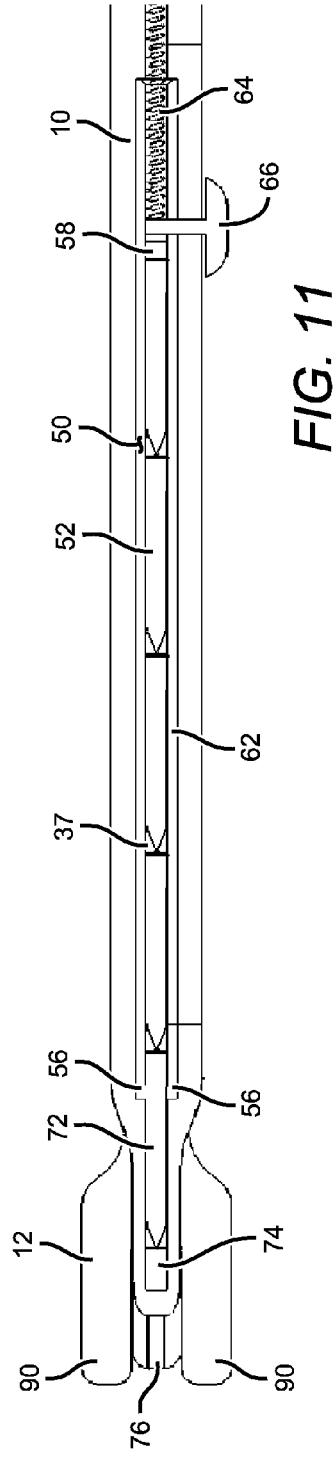

DELIVERY MECHANISM FOR TISSUE HOLDING IMPLANTS

RELATED APPLICATIONS

This application claims the benefit of provisional patent application No. 61/123,077 to Thomas Weisel and Roger Pisarnwongs, filed Apr. 4, 2008.

BACKGROUND OF THE INVENTION

1. Field of the Invention

This invention relates generally to mechanisms designed to facilitate the delivery of tissue holding implants into the human body.

2. Description of the Related Art

During medical procedures such as surgery, it is often necessary to join two or more tissues in approximation until healing has occurred. It is generally important that the doctor be able to perform this task safely and quickly. However, for some procedures, conventional methods of joining tissues can be unsatisfactory.

Septoplastic surgery is an example of such a procedure. During a typical septoplastic procedure, the surgeon will peel the mucosa from each side of the septal cartilage, modify the cartilage as required, and then reattach the mucosa. This is often done with a suture being passed back and forth through the 2 or 3 layers of tissue (mucosa-septum-mucosa or mucosa-mucosa), working alternately through each nostril. This suturing task can sometimes be tedious and time consuming due to swollen tissue and difficult access.

A number of tissue holding means have been devised as an alternative to sutures. For example, a number of one or two-piece tissue holding implants are described in co-pending patent application Ser. No. 12/152,361 by Weisel and Pisarnwongs and assigned to the present assignee. These implants employ various means to hold tissues together once they have been successfully implanted. However, some of these implants may be difficult to deliver to the tissues that need to be joined.

SUMMARY OF THE INVENTION

The present invention is directed to a mechanism for delivering tissue holding implants into the body and through tissues to be held in approximation.

The present delivery mechanism includes a shaft having a tip at its distal end and is adapted to receive at least one tissue holding implant. A wire channel which contains a driving wire is also located within the shaft. An actuating means is arranged such that, when actuated, the driving wire exhibits a proportional longitudinal displacement in the wire channel towards the shaft tip. The mechanism and implants are arranged such that, when the actuating means is actuated, the driving wire engages an implant, conveys it along the shaft's longitudinal axis towards the tip, and forces it through the tip. The implants are oriented such that they lie along or nearly along the shaft's longitudinal axis when being conveyed along the axis.

The mechanism may be used to deliver an implant into tissue that has its own stabilization means, such as bone or a taut tendon. The mechanism may optionally provide its own stabilization means in the form of a jaw and an actuating means, arranged such that, when actuated, the distal end of the jaw is moved towards the tip, such that tissues placed between the jaw and tip are pinned between them. In this case, the delivery mechanism delivers implants through the tip and into the pinned tissues.

These and other features, aspects, and advantages of the present invention will become better understood with reference to the following description and claims.

BRIEF DESCRIPTION OF THE DRAWINGS

FIG. 2 is a plan view (from below) of one possible embodiment of a delivery mechanism per the present invention.

FIG. 4 is a close-up side elevation view of one possible embodiment of a delivery mechanism per the present invention, partially cutaway to show the interior of the mechanism's shaft.

FIG. 5 is a perspective view of a cartridge as might be used with a delivery mechanism per the present invention.

FIGS. 9 and 10 are side elevation views of the distal end of one possible embodiment of a delivery mechanism per the present invention, with FIG. 10 partially cutaway to show the interior of the mechanism's shaft.

FIGS. 11 and 12 are plan views of the distal end of one possible embodiment of a delivery mechanism per the present invention, with FIG. 11 cutaway to show the interior of the mechanism's shaft and FIG. 12 showing a close-up of the distal end.

DETAILED DESCRIPTION OF THE INVENTION

When operated, the present mechanism delivers tissue holding implants through tissues to be held in approximation. The mechanism, which can be adapted for use with a number of different implant types, includes a shaft in which the implants are loaded, and which has a distal tip through which they are ejected. The mechanism is arranged such that, when actuated, implants are conveyed along the shaft's longitudinal axis towards the tip, and then forced through the tip and the tissues to be held, with the implants oriented such that they lie along the shaft's longitudinal axis when being conveyed along the axis, or lie nearly along the axis (i.e., the implants might lie at a small angle with respect to the axis). This serves to decrease the profile of the distal tip, which can be extremely useful when employed in confined areas such as a nostril.

The present mechanism may be used to deliver a tissue holding implant into tissue that has its own stabilization means, such as bone or a taut tendon. An exemplary embodiment of a mechanism suitable for this application is discussed below in relation to FIG. 17.

The mechanism may optionally provide its own stabilization means in the form of a jaw and an actuating means, arranged such that, when actuated, the distal end of the jaw is moved towards the shaft's distal tip, such that tissues placed between the jaw and tip are pinned between them. In this case, the delivery mechanism delivers implants through the shaft tip and into the pinned tissues. This is a preferred embodiment, and is now described.

Figure 3:
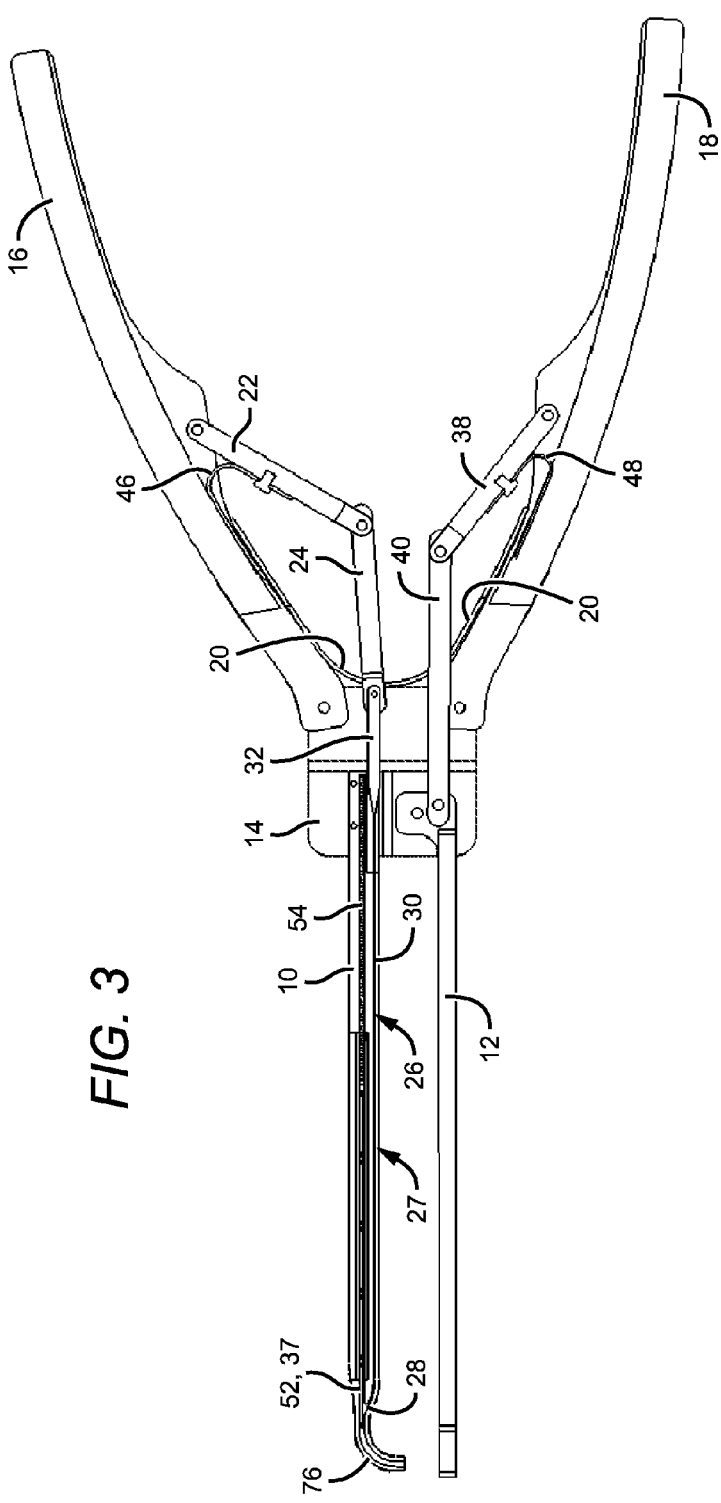
FIG. 3 is a side elevation view of one possible embodiment of a delivery mechanism per the present invention, partially cutaway to show the interior of the mechanism's shaft.

One possible embodiment of a delivery mechanism which includes an opposing jaw is shown in FIGS. 1, 2, 3 and 4, which provide perspective, plan (from below), side elevation and close-up elevation views, respectively (with FIGS. 3 and 4 partially cutaway to show the interior of the mechanism's shaft). The mechanism is shown in a scissor-grip configuration, but it should be noted that a pistol-grip configuration would work as well.

The mechanism consists of a shaft 10 and a jaw 12 coupled to a base 14; one or more tissue holding implants 52 are loaded into the shaft. Also coupled to base 14 is an actuating handle 16, which controls the movement of tissue holding implants loaded into shaft 10 (discussed below), and a lever 18, which manipulates jaw 12.

For this embodiment, actuating handle 16 and lever 18 are held in relative position with a spring 20. A pair of driving links 22 and 24 couple actuating handle 16 to a bendable driving wire 26, which passes through the shaft 10 via a wire channel 27 (which is more clearly seen in FIGS. 8, 10 and 13-14, discussed below). Driving wire 26 consists of a tip 28, a thin bendable shaft 30 and a connecting shaft 32. Actuation (34) of actuating handle 16 results in a proportional longitudinal displacement (36) of the driving wire 26 along the length of shaft 10, which serves to move one of the loaded tissue-holding implants through the shaft via a main channel 37 and eject it through the shaft's distal tip (discussed in detail below). The thin bendable shaft of the driving wire can be made from a nickel-titanium alloy such as NITINOL, for example, which can have the characteristic of super-elasticity, though various plastics and metals might also be suitable, depending on the angle with which the implants are ejected with respect to the shaft.

Another set of driving links 38 and 40 couple lever 18 to jaw 12. Actuation (42) of lever 18 results in proportional movement (44) of jaw 12.

A pair of springs 46 and 48 are implemented to i) maintain the positioning of driving links 22, 24 and 38, 40, respectively, and ii) control the ease (force-wise) with which driving wire 26 and jaw 12 are manipulated.

The mechanism is actuated by squeezing actuating handle 16 and lever 18 together. This preferably results in the following sequence of events: jaw 12 is moved towards shaft 10, such that the tissues through which the implant is to be delivered are captured between the jaw and the shaft tip. Then, the driving wire is displaced along the shaft causing an implant to be ejected from the distal end of shaft 10 and into the tissues.

It is preferable, though not essential, that the spring rate of spring 46 be higher than that of spring 48. This is to ensure that, when the mechanism is actuated, spring 48 collapses before spring 46—causing jaw 12 to close over the tissues before driving wire 26 is displaced.

Figure 1:
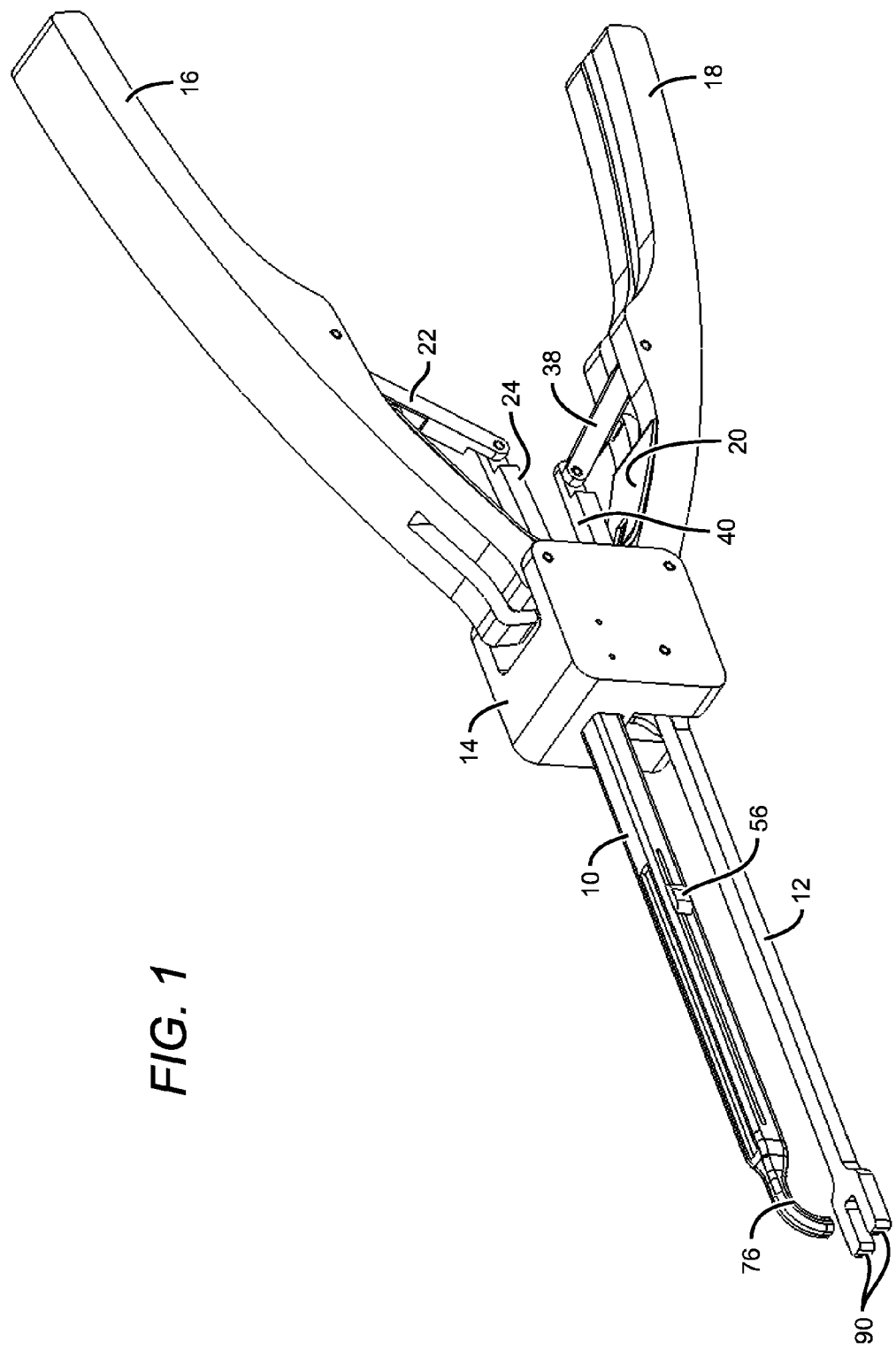
FIG. 1 is a perspective view of one possible embodiment of a delivery mechanism per the present invention.

Note that, though shaft 10 is shown as having a curved distal tip in FIGS. 1-3 (as well as in FIGS. 7-15, discussed below), this is not essential. The shaft tip might alternatively lie along the shaft's longitudinal axis, such that implants are ejected from the tip as a bullet would be from a gun. In this case, the configuration of jaw 12 would need to be changed from that shown in the figures, such that it still moves towards the shaft tip and captures tissues between the jaw and shaft tip when the mechanism is actuated.

Figure 6:
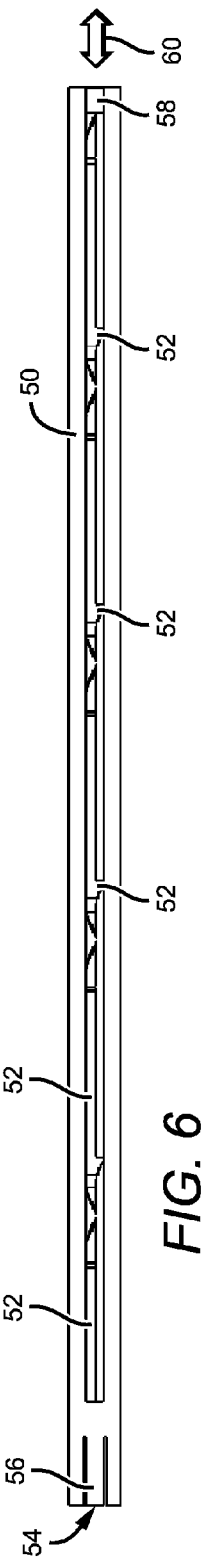
FIG. 6 is a side elevation view of a cartridge as might be used with a delivery mechanism per the present invention.

The implants to be delivered are preferably placed into shaft 10 by means of a cartridge that is loaded into shaft 10 or base 14; FIGS. 5 and 6 show perspective and side elevation views of one possible embodiment of such a cartridge 50. The cartridge houses one or more tissue holding implants 52. In the configuration shown, tissue holding implants 52 are aligned end-to-end length-wise along the longitudinal axis of cartridge 50. When the mechanism is actuated, the implants are translated distally through the cartridge, with the implant at the distal end being ejected from cartridge 50 via an opening 54.

Note that the tissue holding implants can also be arranged in a variety of other orientations without adversely affecting the workings of the device. For example, the implants might alternatively be stacked atop each other perpendicular to the longitudinal axis of the shaft; this possibility is discussed in more detail below.

As will be described in detail below, a spring applies force to the implants within cartridge 50 when the cartridge is loaded into shaft 10. To prevent the implants from being ejected prematurely by the spring force, cartridge 50 may include one or more constraining fingers 56 at its distal end. The appropriate shape and characteristics of the fingers depend on the type of implant being delivered. In the exemplary embodiment shown in FIGS. 5 and 6, constraining fingers 56 are L-shaped and act like deflection beams. The proximal end of the implant would be made slightly larger than the distal end, so that the fingers grab onto the implant's proximal end as it translates distally through the cartridge. The spring force is preferably imparted to the loaded implants via a cartridge ram 58 located at the proximal end of cartridge 50, which is allowed to translate along the length of the cartridge (60). Additional force is applied to the implant via the driving wire in order to move it past the fingers (discussed below).

It is preferable, though not essential, that a cartridge as described above be used. In the absence of a cartridge, implants would be loaded directly into shaft 10. Such a delivery mechanism might be pre-loaded at an assembly facility and delivered to a surgeon ready for use. A delivery mechanism of this sort might be characterized as a disposable device.

Figure 7:
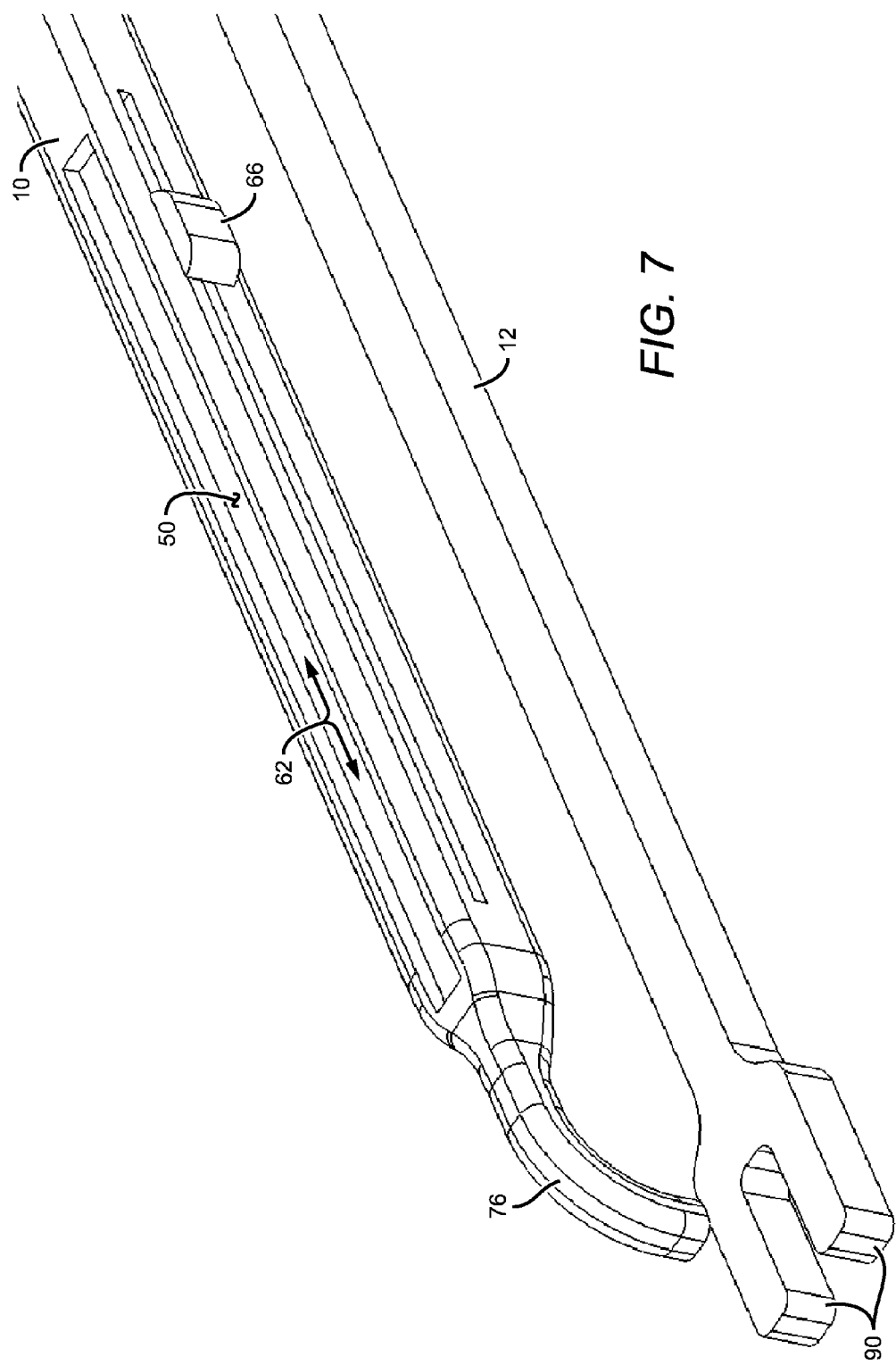
FIGS. 7 and 8 are perspective views of the distal end of one possible embodiment of a delivery mechanism per the present invention, with FIG. 8 partially cutaway to show the interior of the mechanism's shaft.
Figure 8:
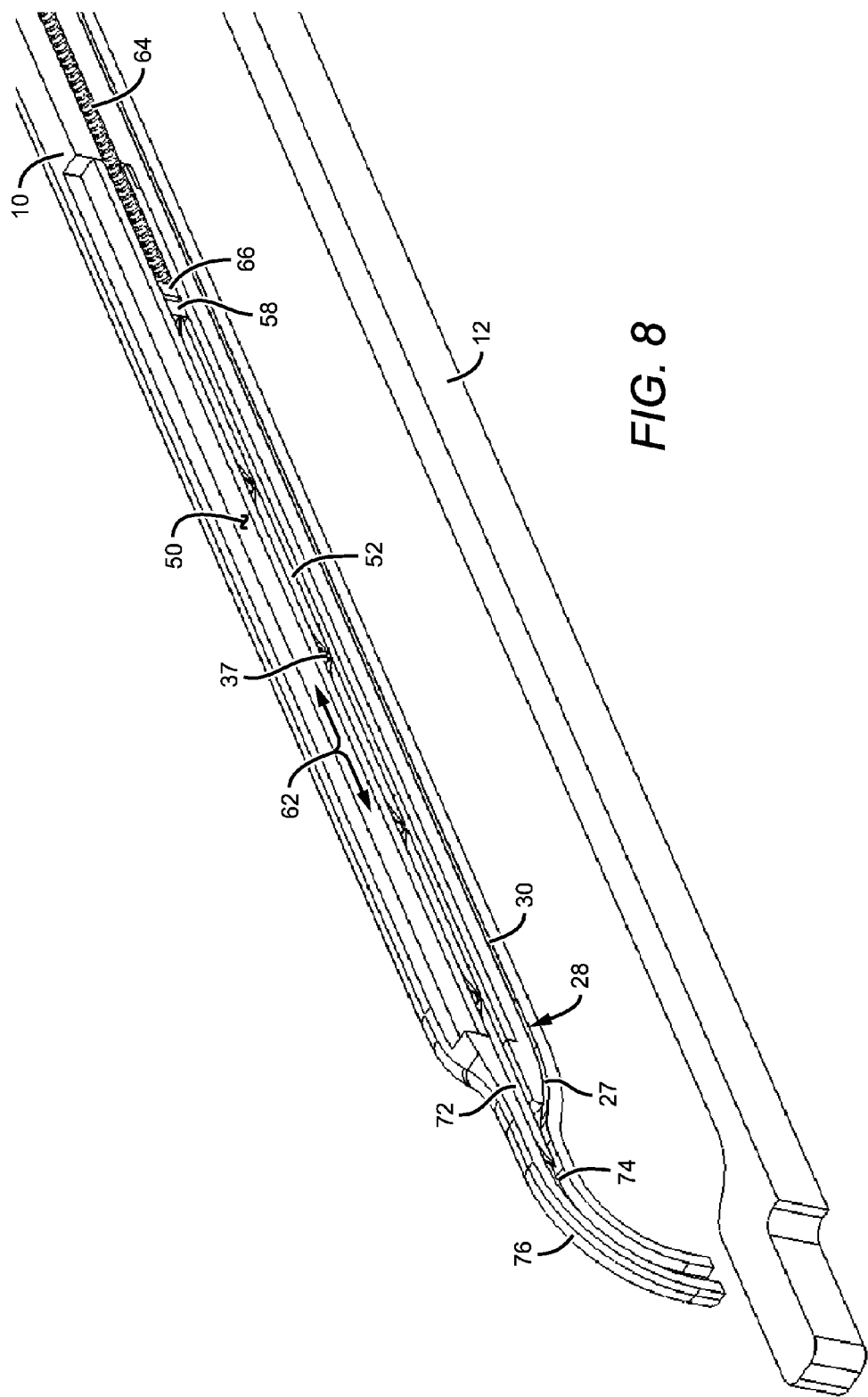
Figure 9:
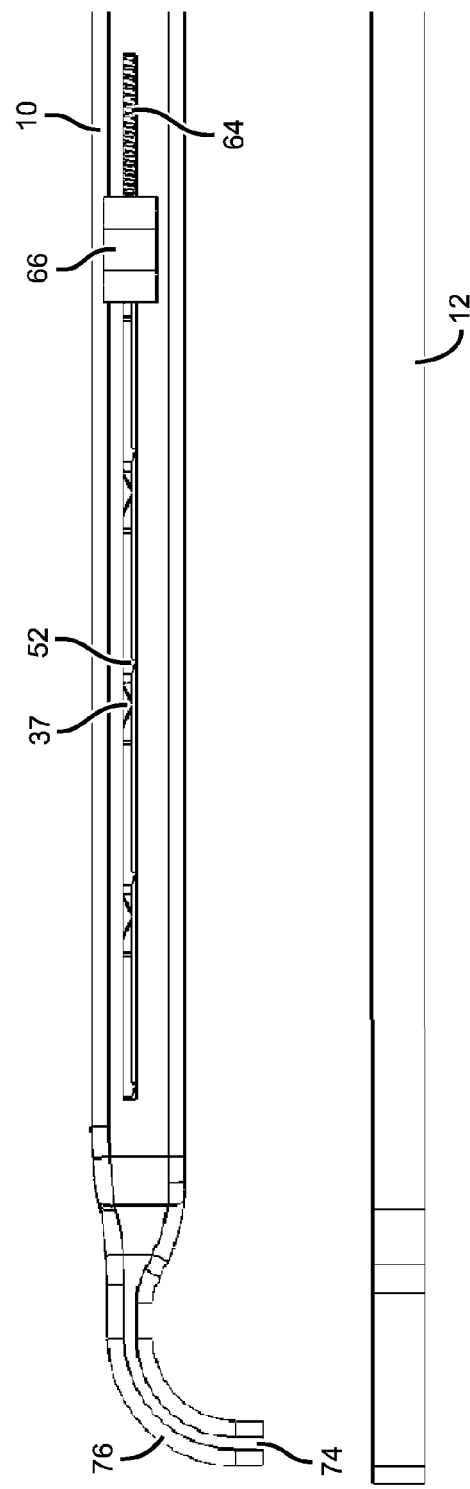
Figure 12:
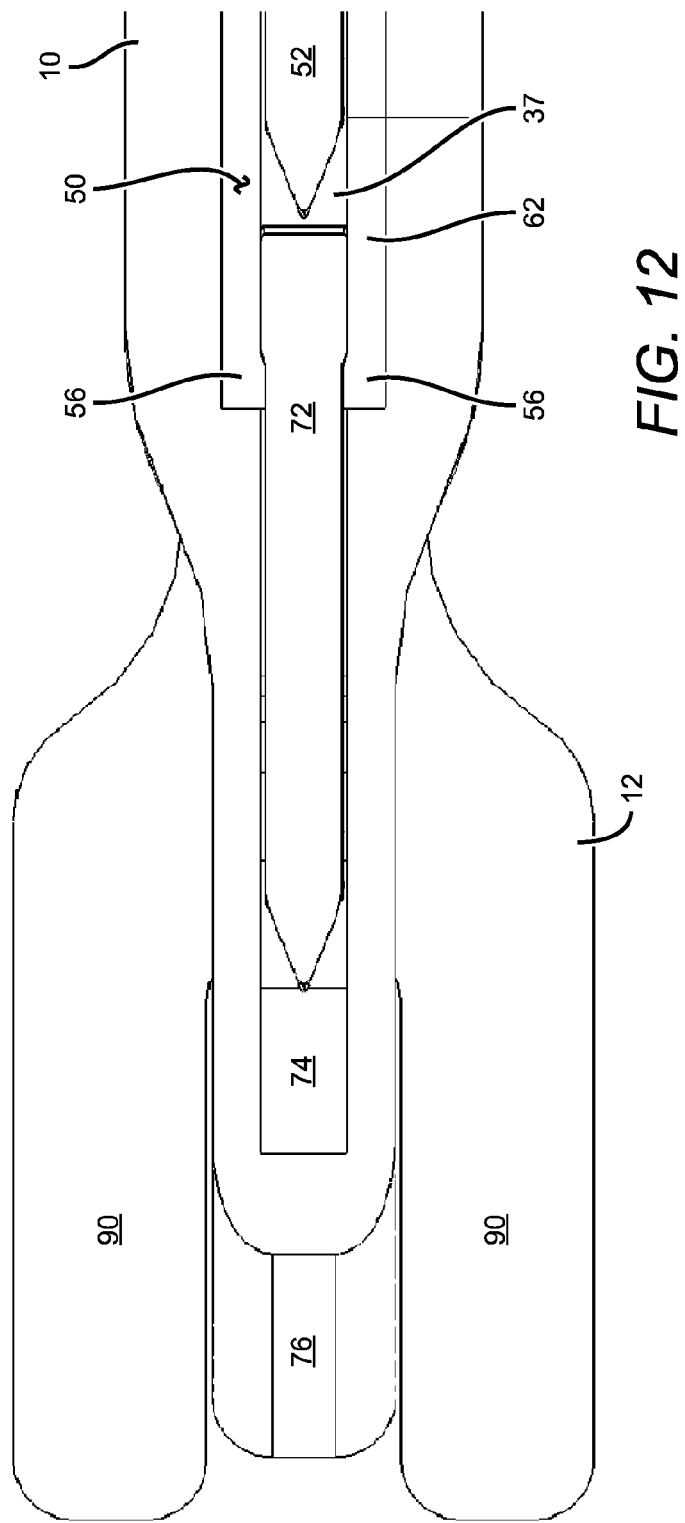

FIGS. 7-12 show the distal end of an exemplary embodiment of the present delivery mechanism. FIGS. 7 and 8 are perspective views, with FIG. 8 being cutaway to show the interior of shaft 10; FIGS. 9 and 10 are side elevation views, with FIG. 10 being cutaway to show the shaft interior; FIGS. 11 and 12 are plan views, with FIG. 11 being cutaway to show the shaft interior and FIG. 12 showing a close-up of the distal end.

In this example, cartridge 50 is inserted into a slot 62 provided in shaft 10, with the major length of the cartridge aligned along the longitudinal axis of shaft 10 in this example; in this arrangement, cartridge 50 serves as the shaft's main channel 37. However, as previously noted, this orientation is not critical and may be different. A spring 64 within shaft 10 is aligned with a ram 66, which is aligned with and forced against cartridge ram 58. A portion of ram 66 preferably protrudes out of the side of the shaft (most clearly seen in FIG. 7), to allow spring 64 to be manually compressed so that cartridge 50 can be loaded into slot 62.

The force from spring 64 is translated to implants 52 via ram 66 and cartridge ram 58. The force from spring 64 and the counterforce resulting from the interaction of constraining fingers 56 and implants 52 should ensure that the two rams remain in contact with each other during use. The two rams can be coupled together mechanically, though this is not essential. The spring force pushes the tissue holding implants distally (70, as shown in FIG. 10) until constraining fingers 56 impede further translation. At this point, the first (most distal) implant 72 has been forced into a channel 74 provided within the curved tip 76 at the distal end of shaft 10.

Figure 13:
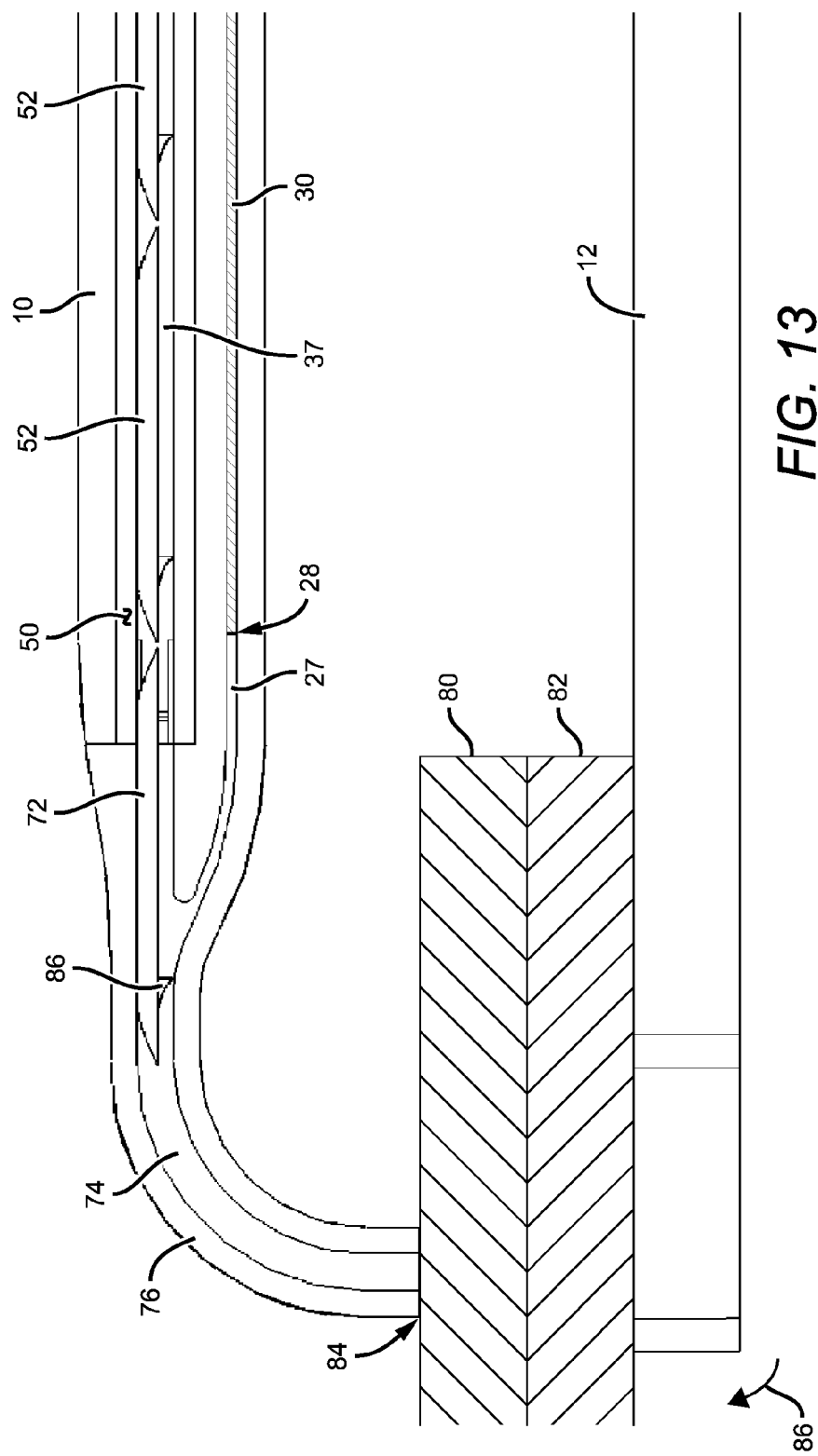
FIGS. 13 and 14 are side elevation views of the distal end of one possible embodiment of a delivery mechanism per the present invention, both partially cutaway to show the interior of the mechanism's shaft, illustrating the use of the mechanism to deliver a tissue holding implant into tissues to be held.
Figure 14:
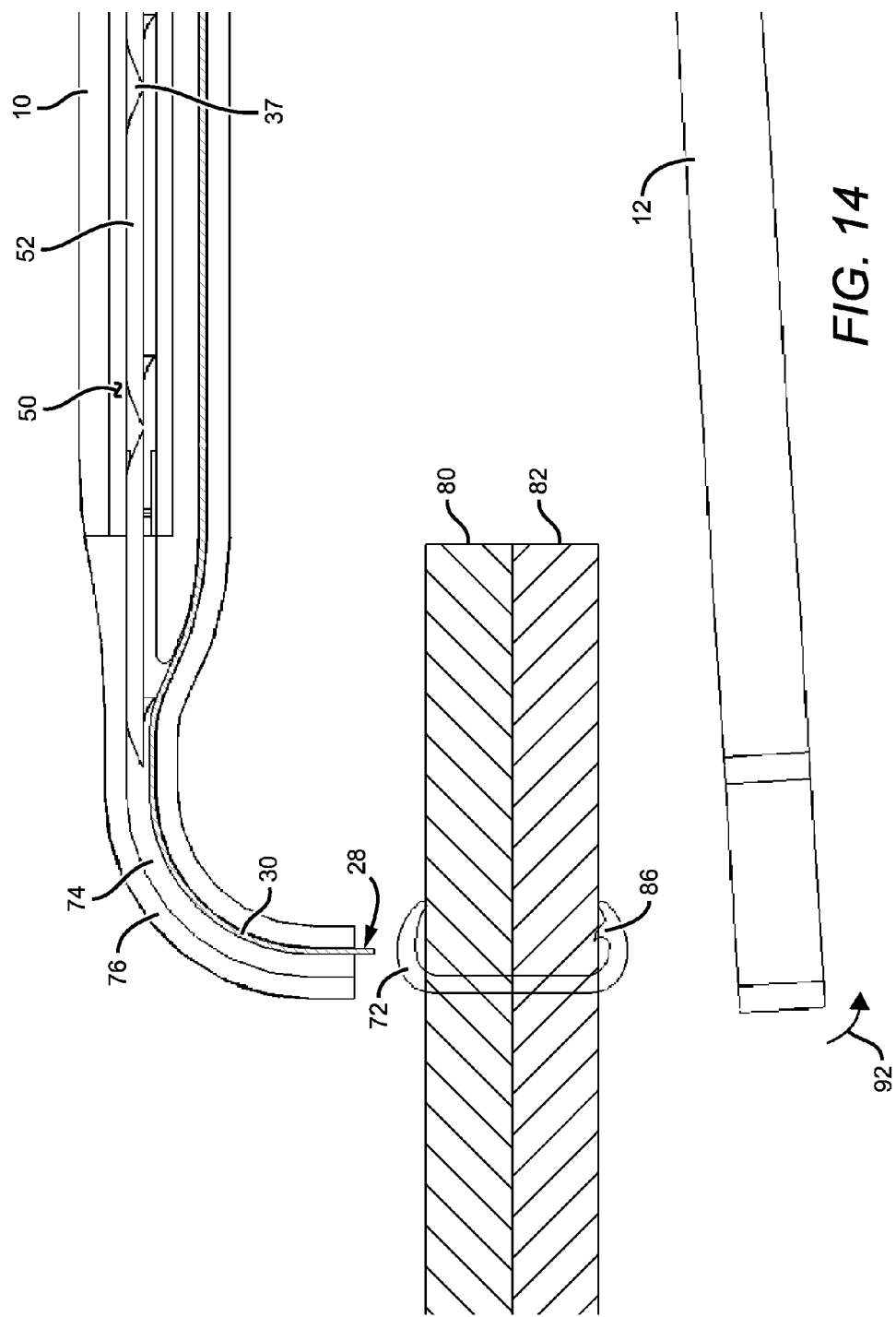

FIGS. 13 and 14 demonstrate the use of the present delivery mechanism to connect two pieces of tissue, 80 and 82. The tissue pieces are placed between the terminus 84 of distal curved tip 76 and jaw 12. Actuation of lever 18 closes jaw 12 over the tissue pieces (86). While tissue pieces 80 and 82 are pinned between terminus 84 and jaw 12, the actuating handle 16 is actuated. This causes the thin bendable shaft 30 of driving wire 26 to translate distally along wire channel 27 provided through shaft 10.

Wire channel 27 merges with channel 74 provided within the shaft's curved tip 76. As shown in FIG. 14, as the driving wire's thin bendable shaft 30 translates distally through wire channel 27, the driving wire's tip 28 eventually engages with the most distal tissue holding implant 72; in this case with a tab 86 protruding from the bottom of the implant. The force applied to implant 72 by bendable shaft 30 overcomes the counterforce provided by constraining fingers 56, thereby forcing the implant past the constraining fingers and through channel 74. As bendable shaft 30 continues to be translated distally, tissue holding device 72 is eventually pushed beyond the terminus 84 of curved tip 76, and it pierces through tissue pieces 80 and 82.

The portion of jaw 12 located beneath the terminus of curved tip 76 preferably includes a gap 90, which allows the leading edge of the tissue holding implant to pass completely through the tissues when delivered.

Once tissue holding implant 72 is positioned appropriately, actuating handle 16 and lever 18 are released. The implant now holds tissues 80 and 82 in approximation, the bendable shaft 30 of the driving wire retracts back into wire channel 27, and another tissue holding implant is forced into the distal position due to the force imparted to the implants by spring 64, via ram 66 and cartridge ram 58. Jaw 12 then releases its hold on tissue pieces 80 and 82 (92).

It should be noted that, in this particular configuration, the tissue holding implant 72 leads the driving wire's tip 28 as the implant is being pushed out of the mechanism. Consequently, the implant pierces the tissue before the driving wire tip. The mechanism might alternately be arranged such that driving wire tip 28 leads the implant 72. In this case, tip 28 would pierce the tissue before the implant.

The present mechanism can be configured to accommodate implants which are bendable or rigid. When the shaft tip is curved, the implants should be bendable enough to ensure that they can successfully negotiate the radius of the curve as they are conveyed around the corner of a curved shaft tip. The implant illustrated in FIGS. 13 and 14 is bendable, and has been 'preformed' such that it wraps around the tissues once it has been completely ejected from the delivery mechanism. Such an implant may be made from a super-elastic or shape memory plastic, or metal. For example, an implant made from a nickel-titanium alloy such as NITINOL can have the characteristic of super-elasticity. Some implant embodiments might alternatively be made from a material which exhibits a shape memory behavior; some NITINOL alloys possess this property. Implants made from a super-elastic or shape memory material are capable of being formed into an initial or 'compressed' shape suitable for insertion into the tissues to be held, and then reverting to a known 'preformed' shape when unconstrained.

Figure 15:
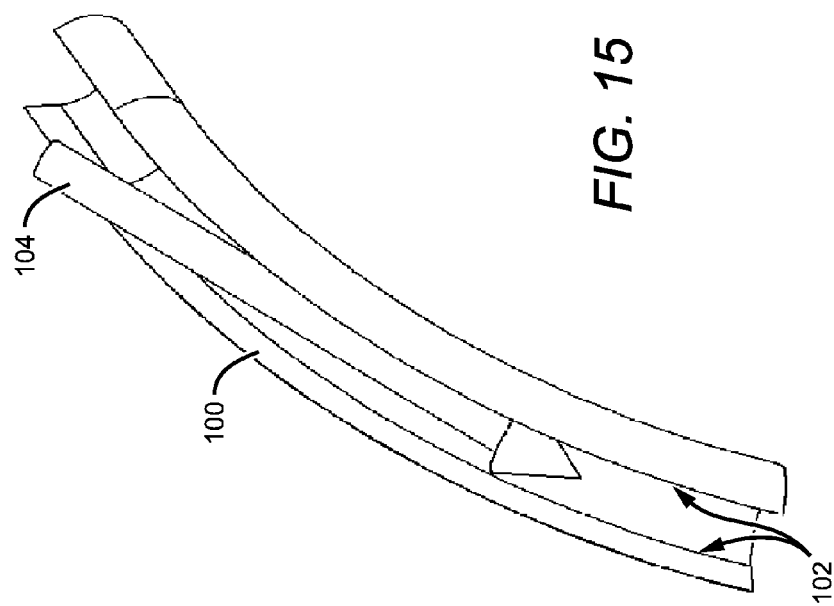
FIG. 15 is a perspective view of a curved tip as might be used with a delivery mechanism per the present invention, which includes a slot arranged to accommodate a rigid implant.

When the implants are rigid, it may be difficult or impossible for them to negotiate the radius of a curved shaft tip. In this case, the curved tip may include a slot through which the proximal end of a rigid implant may protrude as it is forced around the corner of the curved tip. This is illustrated in FIG. 15, which shows just the curved tip 100 and a rigid implant. Tip 100 includes a slot 102 in its upper surface through which the proximal end 104 of the implant can protrude as it is conveyed around the curve. The slot should be wide enough to allow the proximal end of the implant to protrude, yet small enough to ensure that at least a portion of the implant is retained within the curved tip.

Many implant types and configurations could be delivered with a mechanism as described herein. In general, an implant suitable for delivery via the present mechanism would have the following characteristics:

preformed in a shape suitable for holding tissues together once ejected from the mechanism. Alternatively, the implant could be deformable by mechanical or other means after it has been ejected.

includes a feature capable of being engaged by the mechanism's driving wire, such as a tab, a notch, a slot, etc.

rigid enough to withstand the force of the spring 64, as well as the force applied by the driving wire 26. For example, the implants illustrated in FIGS. 21-27 of co-pending patent application Ser. No. 12/152,361 would be well-suited for delivery via the present mechanism. However, many of the other implants described there could also be delivered, though some would require some modification to their profiles.

Suitable implants are made with materials that are biocompatible, and may also be biodegradable. For example, an implant may comprise an absorbable or non-absorbable biocompatible plastic. Alternatively, an implant may comprise a biocompatible metal, such as stainless steel.

Figure 16:
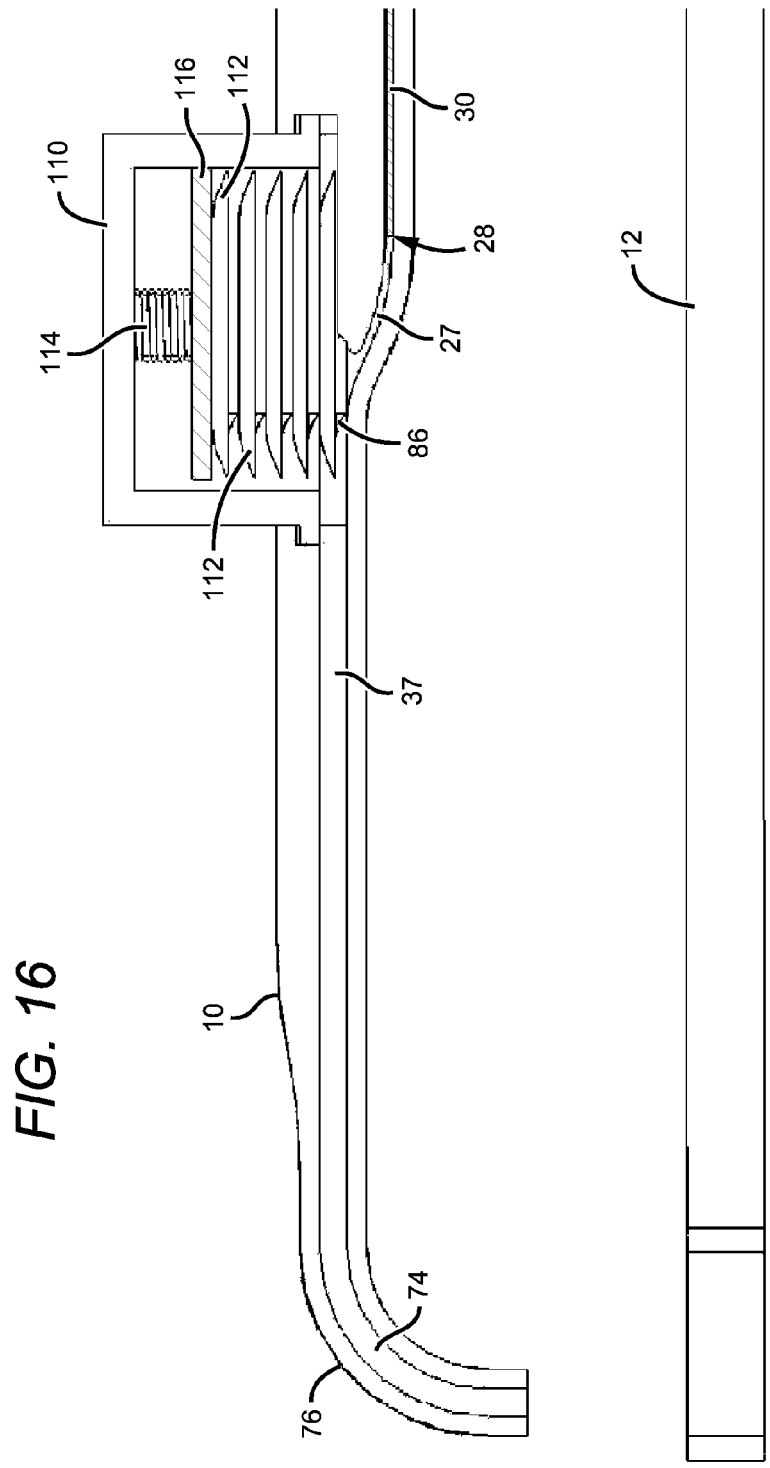
FIG. 16 is a side elevation view of another possible embodiment of a delivery mechanism per the present invention, partially cutaway to show the interior of the mechanism's shaft and cartridge.

As noted above, the implants might alternatively be stacked atop each other such that the stack is approximately perpendicular to the longitudinal axis of the shaft. One possible embodiment of a mechanism configured in this way is shown in FIG. 16. Here, the cartridge 110 houses one or more tissue holding implants 112, a cartridge spring 114, and a cartridge ram 116, with the tissue holding implants stacked atop each other as opposed to being aligned end-to-end. Once the cartridge 110 is inserted into shaft 10, the force from spring 114 pushes the implant at the bottom of the stack into the shaft's main channel 37. The driving wire's bendable shaft 30 can then be used to deploy the implant in a similar manner to that previously described.

Figure 17:
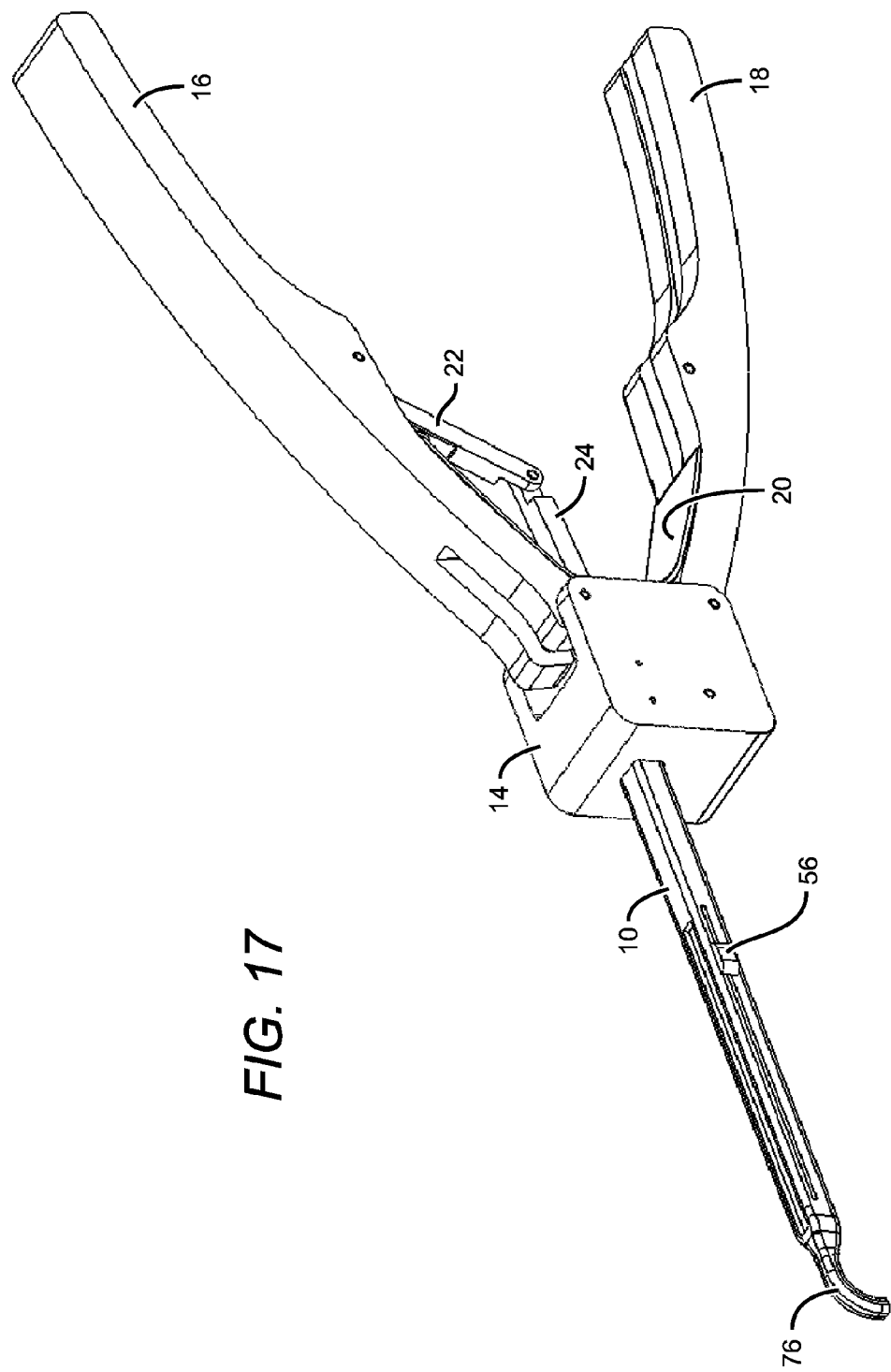
FIG. 17 is a perspective view of another possible embodiment of a delivery mechanism per the present invention, which does not include an opposing jaw.

As noted above, the present mechanism may be used to deliver a tissue holding implant into tissue that has its own stabilization means, such as bone or a taut tendon. An exemplary embodiment of a mechanism suitable for this application is shown in FIG. 17. The mechanism is similar to that shown in FIG. 1, in that implants are conveyed down shaft 10 to a tip 56 via a driving wire which is displaced longitudinally when the mechanism is actuated. Here, however, a jaw is not used to pin tissues to the shaft tip. Rather, the implant is delivered into bone or soft tissue that is held in place by some other method, so that an opposing jaw is not needed.

In the exemplary embodiments illustrated herein, the mechanism's shaft and tip are designed such that the tissue holding implants are oriented so that they lie along the shaft's longitudinal axis, and then are ejected at an angle with respect to the shaft. In the illustrated embodiments, the firing angle is approximately 90°, though other angles—including 0°—could also be used.

However, for all embodiments, the mechanism is arranged such that the implants lie along or nearly along the shaft's longitudinal axis when being conveyed along the axis. When so arranged, the profile of the distal tip can be reduced in comparison with other devices that require the implant to be loaded at the same angle at which it is fired.

The embodiments of the invention described herein are exemplary and numerous modifications, variations and rearrangements can be readily envisioned to achieve substantially equivalent results, all of which are intended to be embraced within the spirit and scope of the invention as defined in the appended claims.

We claim:

1. A delivery mechanism for tissue holding implants, comprising:
    a base;
    a shaft coupled to said base at a proximal end of said shaft and having a curved tip at a distal end of said shaft;
    a cartridge into which a plurality of tissue holding implants are loaded, said shaft including a slot adapted to receive said cartridge, said cartridge arranged such that, when loaded and placed within said shaft, said implants lie end-to-end lengthwise along a longitudinal axis of said shaft, said cartridge serving as a main channel through which said tissue holding implants may be translated distally;
    a wire channel within said shaft which remains separate from said main channel until said wire channel merges with said main channel at the distal end of said shaft, said wire channel containing a driving wire;
    a jaw coupled to said base at a proximal of said jaw end and which extends approximately parallel to and spaced apart from said shaft, wherein a distal end of said jaw is located approximately below said curved tip;
    a spring-loaded ram arranged to apply a force to said implants loaded in said cartridge so as to push said implants towards a distal end of said cartridge;
    a constraining mechanism at the distal end of said cartridge arranged to inhibit the translation of an implant pushed by said ram beyond said constraining mechanism;
    a first actuating mechanism coupled to said base and arranged such that, when said first actuating mechanism is actuated, the distal end of said jaw is moved towards said curved tip; and
    a second actuating mechanism coupled to said base and arranged such that, when said second actuating mechanism is actuated, the distal tip of said driving wire exhibits a proportional longitudinal displacement down said wire channel towards said curved tip;
    said delivery mechanism arranged such that tissues placed between the distal end of said jaw and said curved tip are pinned between said jaw and said curved tip when said first actuating mechanism is actuated;
    said delivery mechanism and implants arranged such that a distal end of said driving wire engages a distal-most implant in said cartridge only where said main channel and wire channels merge and forces said distal-most implant past said constraining mechanism, through said curved tip and through said pinned tissues when said second actuating mechanism is actuated, such that said distal-most implant is ejected from said tip at a non-zero angle with respect to said longitudinal axis of said shaft.

2. The mechanism of claim 1, wherein said plurality of tissue holding implants are bendable.

3. The mechanism of claim 1, wherein said plurality of tissue holding implants are rigid.

4. The mechanism of claim 1, wherein each of said implants includes a tab, notch or slot configured to be engaged by said driving wire.

5. The mechanism of claim 1, wherein a portion of said spring-loaded ram protrudes from said shaft to allow said ram to be manually compressed to facilitate installing said cartridge into said slot.

6. The mechanism of claim 1, wherein said cartridge includes a cartridge ram at a proximal end of said cartridge, said spring-loaded ram arranged to apply a force to said cartridge ram which in turn applies said force to said implants loaded in said cartridge so as to push said implants towards a distal end of said cartridge.

7. The mechanism of claim 1, wherein said jaw includes a gap at said distal end of said jaw which allows the leading edge of an implant being delivered to pass completely through said pinned tissues when delivered.

8. The mechanism of claim 1, wherein the proximal end of said jaw is attached to said base at a first pivot point such that said jaw can move up and down with respect to said base.

9. The mechanism of claim 8, wherein said first actuating mechanism comprises a lever attached to said base at a second pivot point such that said lever can move up and down with respect to said base, further comprising one or more driving links coupled between said lever and said jaw such that moving said lever causes said jaw to pivot about said first pivot point.

10. The mechanism of claim 1, wherein said second actuating mechanism comprises a lever attached to said base at a pivot point such that said lever can move up and down with respect to said base, further comprising one or more driving links coupled between said lever and said driving wire such that moving said lever causes a proportional longitudinal displacement of said driving wire in said wire channel.

11. The mechanism of claim 1, wherein the proximal end of said jaw is attached to said base at a first pivot point such that said jaw can move up and down with respect to said base;
    said first actuating mechanism comprising a first lever attached to said base at a second pivot point such that said first lever can move up and down with respect to said base, further comprising one or more driving links coupled between said first lever and said jaw such that moving said first lever causes said jaw to pivot about said first pivot point, and
    said second actuating mechanism comprising a second lever attached to said base at a third pivot point such that said second lever can move up and down with respect to said base, further comprising one or more driving links coupled between said second lever and said driving wire such that moving said second lever causes a proportional longitudinal displacement of said driving wire in said wire channel.

12. The mechanism of claim 11, wherein said first and second levers form a scissors grip, such that said first and second actuating mechanism are actuated by squeezing said levers together.

13. The mechanism of claim 12, further comprising one or more springs arranged such that, as said levers are being squeezed together, said first actuating mechanism is actuated before said second actuating mechanism.

* * * * *